United States Patent
Haraguchi et al.

(10) Patent No.: US 9,848,757 B2
(45) Date of Patent: Dec. 26, 2017

(54) ENDOSCOPE AND ENDOSCOPE SYSTEM

(71) Applicant: PANASONIC CORPORATION, Osaka (JP)

(72) Inventors: Naoyuki Haraguchi, Saga (JP); Yousuke Kawauchi, Fukuoka (JP); Tooru Tanaka, Fukuoka (JP); Hiroshi Nagayasu, Fukuoka (JP); Ken Shimonosono, Fukuoka (JP); Yasuyuki Takano, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 271 days.

(21) Appl. No.: 14/471,407

(22) Filed: Aug. 28, 2014

(65) Prior Publication Data

US 2015/0062316 A1    Mar. 5, 2015

(30) Foreign Application Priority Data

Aug. 30, 2013    (JP) .................................. 2013-180395

(51) Int. Cl.
A62B 1/04    (2006.01)
A61B 1/00    (2006.01)
(Continued)

(52) U.S. Cl.
CPC ...... *A61B 1/00096* (2013.01); *A61B 1/00009* (2013.01); *A61B 1/0011* (2013.01);
(Continued)

(58) Field of Classification Search
CPC ............ A61B 1/00096; A61B 1/00009; A61B 1/00165; A61B 1/053; A61B 1/0011; G02B 23/243; G02B 27/0006; G02B 7/025
(Continued)

(56) References Cited

U.S. PATENT DOCUMENTS 6,134,056 A * 10/2000 Nakamuka ............... G02B 9/04
                                                    359/660
2002/0128535 A1* 9/2002 Kikuchi ................. A61B 1/042
                                                    600/101
(Continued)

FOREIGN PATENT DOCUMENTS

JP    2004-094043    3/2004
JP    3737848    1/2006

OTHER PUBLICATIONS

Extended European Search Report for European Application No. 14182720.4 dated Jan. 8, 2015.

*Primary Examiner* — Jared Walker
(74) *Attorney, Agent, or Firm* — Greenblum & Bernstein, P.L.C.

(57) ABSTRACT

An endoscope having an insertion portion to be inserted into an object to be observed, includes: a substantially tubular holder member mounted to the insertion portion and having an open front end portion including a shoulder surface surrounded by an axial wall; a lens barrel holding an objective lens system and received in the holder member; and a light-transmissive closure member fitted into a front opening defined by the axial wall, and fixed to the front opening by a bonding agent interposed between an outer circumferential surface of the closure member and an opposing inner circumferential surface of the open front end portion of the holder member, wherein a space axially adjoining the shoulder surface is defined between an outer circumferential surface of a front end portion of the lens barrel and an opposing inner circumferential surface of the holder member.

10 Claims, 8 Drawing Sheets

(51) Int. Cl.
*A61B 1/05* (2006.01)
*G02B 7/02* (2006.01)
*G02B 23/24* (2006.01)
*G02B 27/00* (2006.01)

(52) U.S. Cl.
CPC .......... *A61B 1/00165* (2013.01); *A61B 1/053* (2013.01); *G02B 7/025* (2013.01); *G02B 23/243* (2013.01); *G02B 27/0006* (2013.01)

(58) Field of Classification Search
USPC .......................................................... 348/65
See application file for complete search history.

(56) References Cited

U.S. PATENT DOCUMENTS

| | | | |
|---|---|---|---|
| 2010/0022841 A1* | 1/2010 | Takahashi ............ | A61B 1/0008 600/162 |
| 2012/0029290 A1* | 2/2012 | Nishijima .......... | A61B 1/00137 600/156 |
| 2012/0226104 A1* | 9/2012 | Ikeda ................. | A61B 1/00091 600/129 |
| 2012/0257028 A1* | 10/2012 | Yamamoto ........... | G02B 23/243 348/65 |

\* cited by examiner

ENDOSCOPE AND ENDOSCOPE SYSTEM

TECHNICAL FIELD

The present invention relates to an endoscope and an endoscope system for capturing an image of an inside of an object that cannot be observed directly from outside.

BACKGROUND OF THE INVENTION

Endoscopes are widely used in the medical field and industrial field for capturing an image of an inside of a patient's body or capturing an image of an inside of a device or a structure. With regard to such endoscopes, it has been known to make a configuration such that, in an insertion portion of the endoscope that is to be inserted into an inside of an object to be observed, an objective lens system causes the light from a region to be imaged to be focused on a light receiving surface of an image sensor so that the light is converted to an electrical signal, which in turn is transmitted via a signal cable to an external image processing device or the like as a video signal. Such an insertion portion is required to have a sufficient sealing property for ensuring physical protection and waterproofness when the endoscope is used or at the time of maintenance.

In a case where the insertion portion of the endoscope includes a cover lens mounted to the distal end of the main body thereof so as to be exposed on an outer surface, for example, the sealing structure for the insertion portion of the endoscope may include a silicon-based bonding agent applied from an outer surface side to fill the space between the cover lens and the distal end of the main body to thereby prevent entrance of water or the like into an inside of the endoscope through the part where the cover lens is attached to the distal end of the main body (see JP3737848B2, for example).

In the conventional technology described in JP3737848B2, if a portion (excess portion) of the bonding agent applied to firmly fix the cover lens enters an optical path forming part (for example, an optical path between the cover lens and another lens disposed behind the cover lens) in the endoscope, a problem may arise that the bonding agent can interfere with the incident light (object image) traveling toward the image sensing device. To prevent the undesired entrance of the bonding agent, it may be conceived to reduce the amount of bonding agent applied or to use a bonding agent having a relatively high viscosity, but in these cases, it would become difficult to completely fill the gap between the cover lens and the distal end of the main body with the bonding agent, and this can result in a reduced sealing performance.

The present invention is made to solve the aforementioned problems in the prior art, and a primary object of the present invention is to provide an endoscope and an endoscope system which, in a structure where a light-transmissive closure member is fixed by a bonding agent to a distal end (front) opening of an insertion portion that is to be inserted into an inside of an object to be observed, can prevent entrance of the bonding agent into an optical path forming part defined at the rear of the closure member without reducing the performance of the bonding agent to seal the opening.

SUMMARY OF THE INVENTION

To achieve the above object, one aspect of the present invention provides an endoscope having an insertion portion to be inserted into an object to be observed, including: a substantially tubular holder member mounted to the insertion portion and having an open front end portion including a shoulder surface surrounded by an axial wall; a lens barrel received in the holder member; an objective lens system held by the lens barrel; and a light-transmissive closure member fitted into a front opening defined by the axial wall of the holder member, and fixed to the front opening by a bonding agent interposed between an outer circumferential surface of the closure member and an opposing inner circumferential surface of the open front end portion of the holder member, wherein a space axially adjoining the shoulder surface is defined between an outer circumferential surface of a front end portion of the lens barrel and an opposing inner circumferential surface of the holder member.

The endoscope according to the first aspect of the present invention makes it possible, in a structure where a light-transmissive closure member is fixed by a bonding agent to a distal end (front) opening of an insertion portion that is to be inserted into an inside of an object to be observed (namely, to a front end part of a cylindrical hole of the holder member provided to the insertion portion), to prevent entrance of the bonding agent into an optical path forming part defined at the rear of the closure member (namely, an optical path between the closure member and an objective lens system disposed at the rear of the closure member) without reducing the performance of the bonding agent to seal the opening.

The space between the outer circumferential surface of the front end portion of the lens barrel and the opposing inner circumferential surface of the holder member may be defined either by an increased diameter portion provided on the inner circumferential surface of the holder member or by a reduced diameter portion provided on the outer circumferential surface of the front end portion of the lens barrel. However, since the holder member usually has a wall thickness larger than that of the lens barrel, the space can be formed more easily by providing an increased diameter portion to the inner circumferential surface of the holder member.

In one embodiment, the bonding agent that has entered the space between the outer circumferential surface of the front end portion of the lens barrel and the opposing inner circumferential surface of the holder member bonds the outer circumferential surface of the front end portion of the lens barrel and the opposing inner circumferential surface of the holder member to each other.

According to this arrangement, the bonding agent that has entered the space between the outer circumferential surface of the front end portion of the lens barrel and the opposing inner circumferential surface of the holder member contributes to stably fixing the lens barrel (objective lens system) to the holder member.

The axial wall of the holder member may be provided with at least one recess on an inner circumferential surface thereof such that the at least one recess extends over an axial extent of the axial wall.

According to this arrangement, when the closure member is fixed to the front opening of the holder member, the at least one recess serves as an air vent, and this prevents the bonding agent from being pushed out by the air exiting to the outside from inside the holder member through the space between the outer circumferential surface of the closure member and the inner circumferential surface (bonding area) of the open front end portion of the holder member.

Preferably, the outer circumferential surface of the closure member and the opposing inner circumferential surface of the open front end portion of the holder member are given a shape to engage each other so as to prevent rotation of the closure member relative to the holder member.

According to this arrangement, rotation of the closure member relative to the holder member (closure member fitting portion), which could cause chipping or peeling of the bonding agent interposed between the outer circumferential surface of the closure member and the opposing inner circumferential surface of the open front end portion of the holder member, can be prevented easily.

Further, the lens barrel may be received in the holder member such that a front end of the lens barrel is displaced axially rearward from the shoulder surface of the holder member and a gap is provided between a rear surface of the closure member abutting the shoulder surface and the front end of the lens barrel.

According to this arrangement, the gap ensures that the closure member can be fitted into the front opening of the holder member without interfering with the lens barrel (objective lens system) received in the holder member.

Further preferably, the holder member is provided with a side opening to expose an outer circumferential surface of the lens barrel such that the lens barrel in the holder member can be accessible for position adjustment.

According to this arrangement, the position of the lens barrel (objective lens system) is enabled to be adjusted easily in the fore and aft direction.

In another aspect of the present invention, there is provided an endoscope system, including: the foregoing endoscope; and an image processing device that processes an image provided by the endoscope.

BRIEF DESCRIPTION OF THE DRAWINGS

Now the present invention is described in the following in terms of preferred embodiments thereof with reference to the appended drawings, in which.

DETAILED DESCRIPTION OF THE PREFERRED EMBODIMENTS

In the following, an embodiment of the present invention will be described in detail with reference to the drawings. It is to be noted that the directions referred to in the following description are basically in accordance with those shown in FIG. 1. Namely, "up" and "down" respectively correspond to an upper side and a lower side of a video processor 3, and "front (distal)" and "rear" respectively correspond to an insertion portion 5 side and a plug portion 6 side of an endoscope 2.

Figure 1:
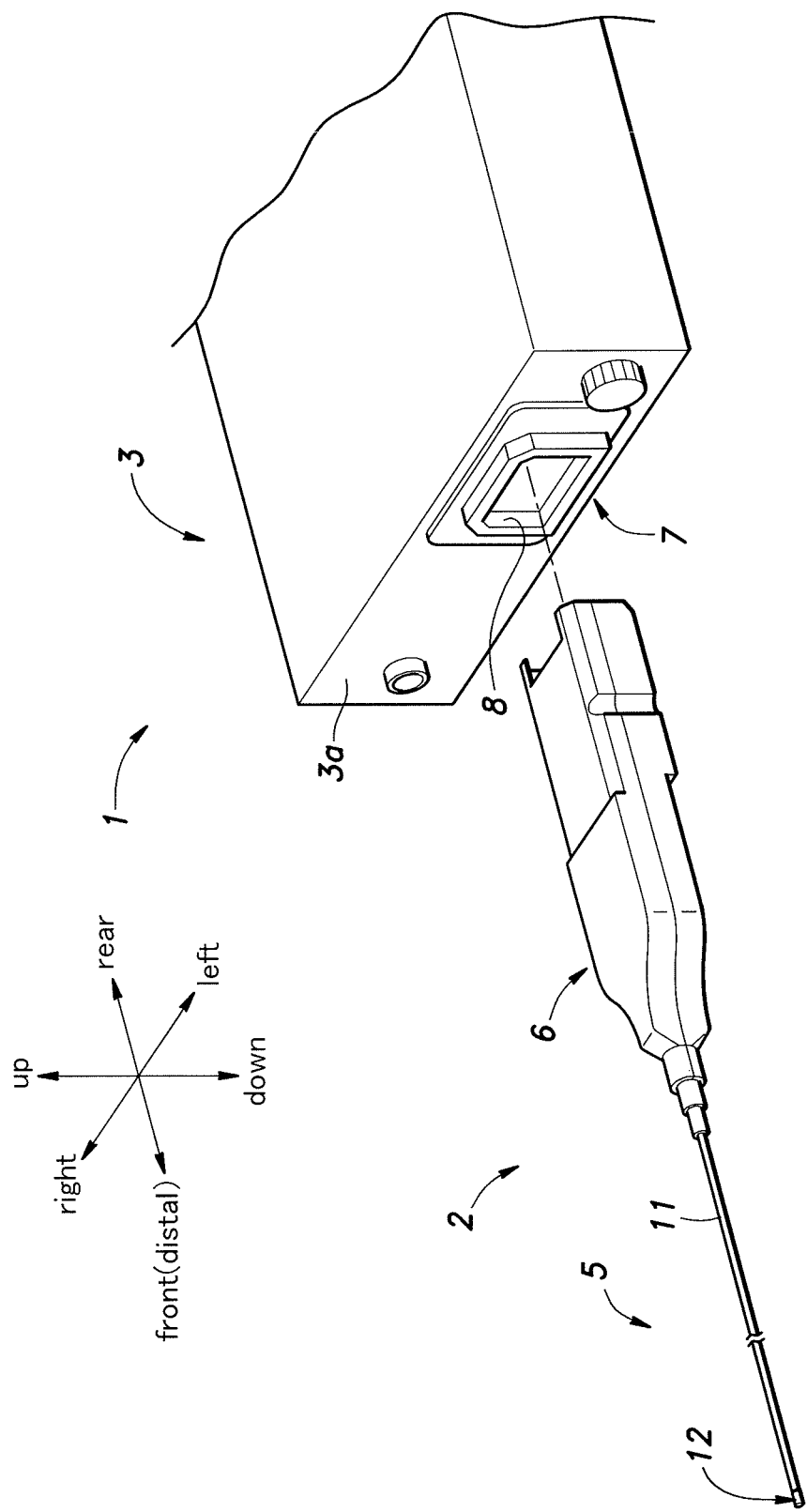
FIG. 1 is a diagram showing an overall structure of an endoscope system utilizing an endoscope according to an embodiment of the present invention.
Figure 2:
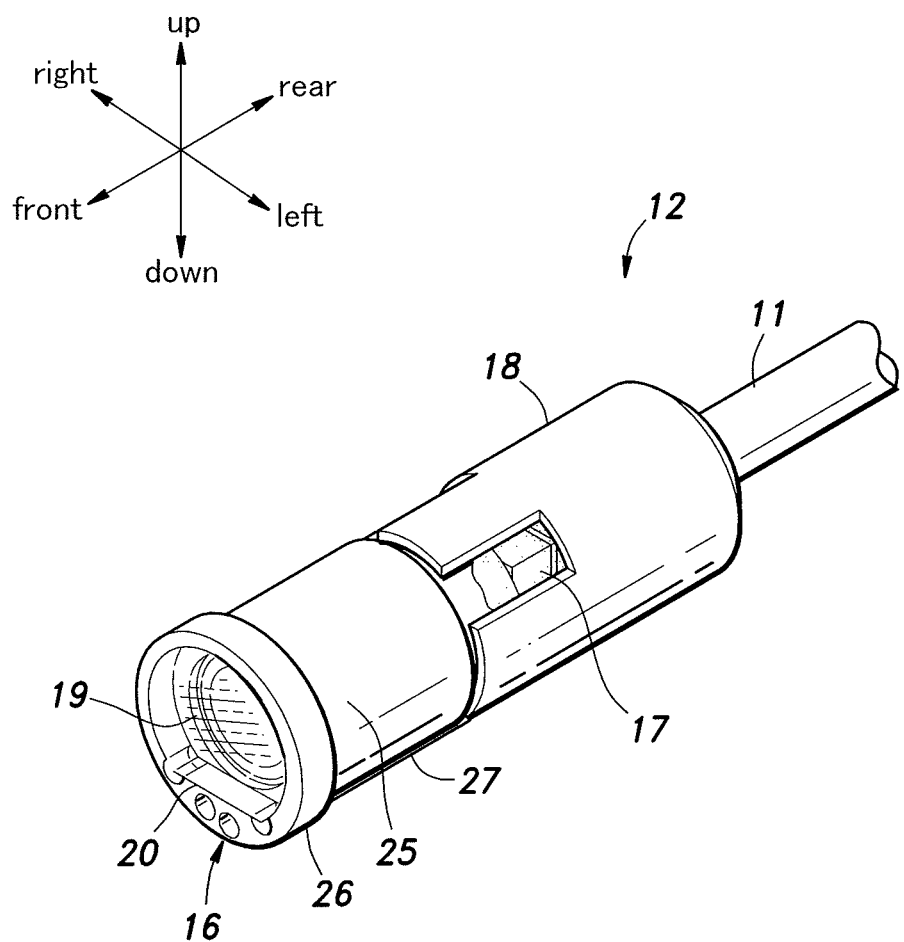
FIG. 2 is a perspective view of an insertion portion distal end of the endoscope.

FIG. 1 is a diagram showing an overall structure of an endoscope system 1 utilizing an endoscope 2 according to an embodiment of the present invention, and FIG. 2 is a perspective view of an insertion portion distal end 12 of the endoscope 2.

As shown in FIG. 1, the endoscope system 1 mainly consists of an endoscope 2, which is a flexible scope for medical use, and a video processor (image processing device) 3 for performing known image processing, etc. on the still images and moving images obtained by capturing images of an inside of an object to be observed (in this embodiment, a human body). The endoscope 2 includes an insertion portion 5 extending substantially in the fore and aft direction so as to be inserted into an inside of an object to be observed and a plug portion 6 connected to a rear part of the insertion portion 5.

The video processor 3 includes a socket portion 7 opening out in a front wall 3a of the video processor 3. The plug portion 6 of the endoscope 2 is inserted into the socket portion 7, whereby electric power and various signals (video signal, control signal, etc.) can be transmitted and received between the endoscope 2 and the video processor 3.

The insertion portion 5 has a relatively small outer diameter (in this embodiment, the maximum outer diameter is 1.8 mm). The insertion portion 5 includes a flexible transmission cable 11 whose rear end is connected to the plug portion 6 and an insertion portion distal end 12 provided at the front end of the transmission cable 11. The transmission cable 11 has a substantially circular cross section and has a known structure formed of bundled electric wires each including a conductor covered with an insulator and a protection film, whereby the transmission cable 11 constitutes a transmission path for the electric power and various signals transmitted to and received from the insertion portion distal end 12.

As shown in FIG. 2, the insertion portion distal end 12 includes, as main parts thereof, a lens holder (holder member) 16 receiving a lens unit 15 (see FIG. 3) therein, an image sensor 17 supported by the lens holder 16 at the rear of the lens unit 15, and a metallic rear cover 18 that covers the image sensor 17 and the distal end of the transmission cable 11 connected with the image sensor 17. The lens unit 15 constitutes an objective lens system of the endoscope 2. The lens holder 16 is positioned at the distal end of the insertion portion 5 (or in the vicinity thereof) so that the incident light can be readily admitted. Further, as described in detail later, an opening on the distal end side of the lens holder 16 is closed by a light-transmissive cover glass (closure member) 19 made of an optical material (glass, resin, etc.).

The cover glass 19 has a substantially circular plate-like shape with a lower part thereof being cut straight to form a deformation part 20. As the cover glass 19 is not formed to be perfectly circular as seen in the front view but includes the deformation part 20 in a part thereof and the inner circumferential surface of the surrounding wall of the lens holder 16 is given a shape complementary to that of the outer circumferential surface of the cover glass 19, rotation of the cover glass 19 relative to the lens holder 16 can be prevented easily. Namely, the outer circumferential surface of the cover glass 19 and the opposing inner circumferential surface of the open front end portion of the lens holder 16 are shaped to engage each other so as to prevent rotation of the cover glass 19 relative to the lens holder 16. Such rotation of the cover glass 19 could cause chipping or peeling of a later-described bonding agent interposed between the outer circumferential surface of the cover glass 19 and the inner circumferential surface of the lens holder 16 and thus reduce the sealing performance. Further, the deformation part 20 formed by cutting a lower part of the cover glass 19 straight also has an advantage that it creates a space for arranging later-described illumination windows 61 (see FIG. 6).

Figure 3:
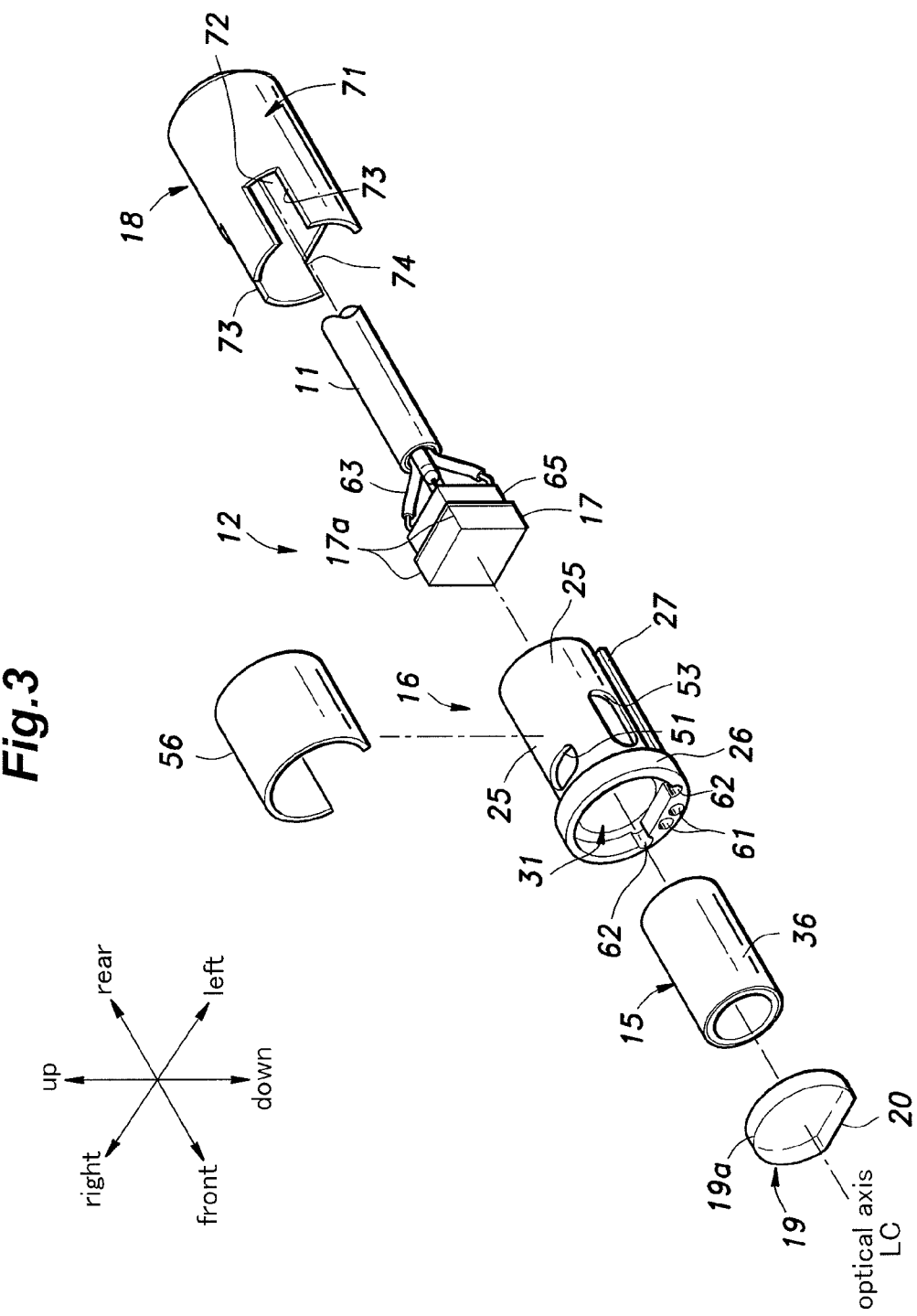
FIG. 3 is an exploded perspective view of the insertion portion distal end of the endoscope.
Figure 4:
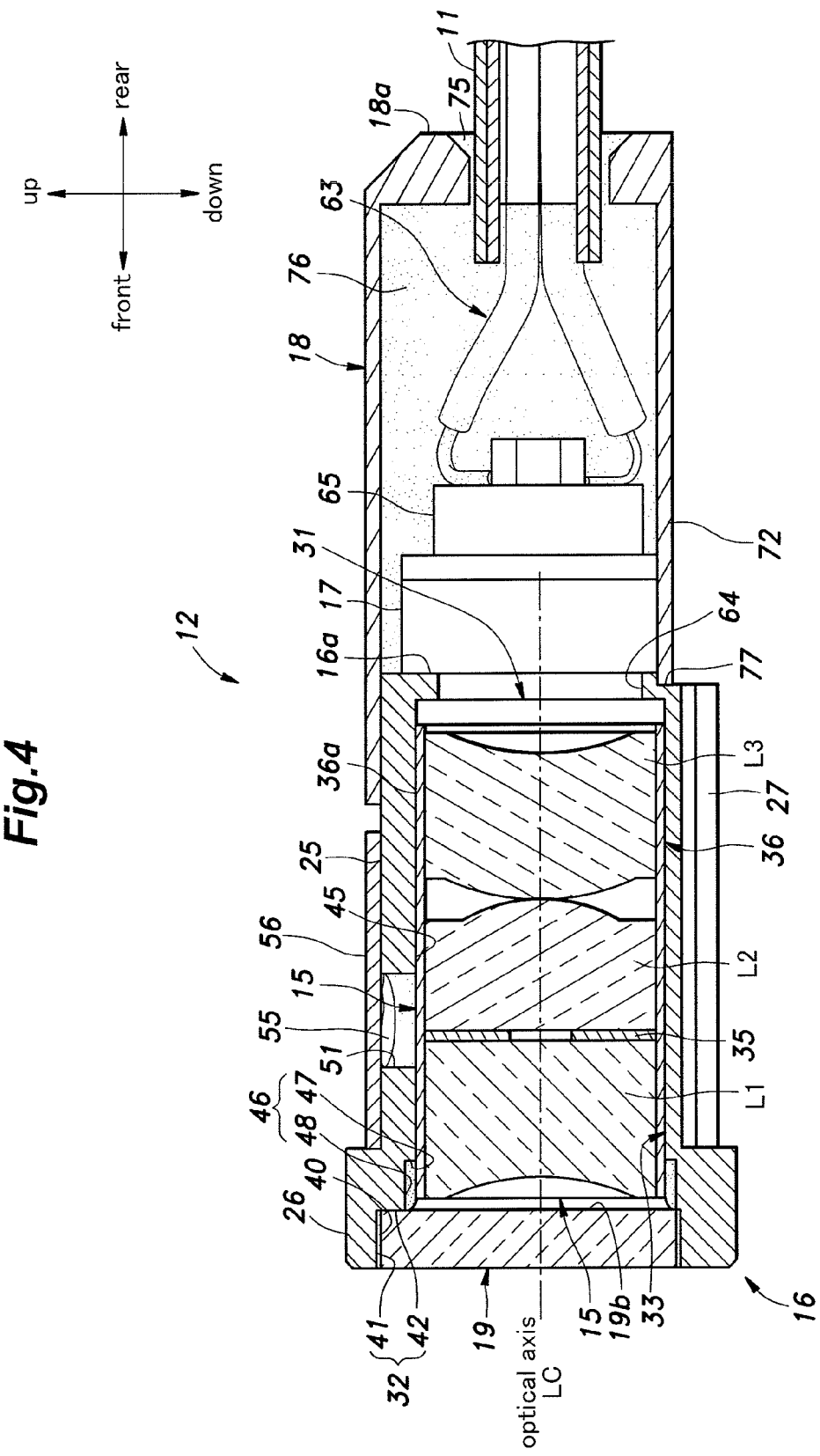
FIG. 4 is a vertical cross-sectional view of the insertion portion distal end of the endoscope.
Figure 5:
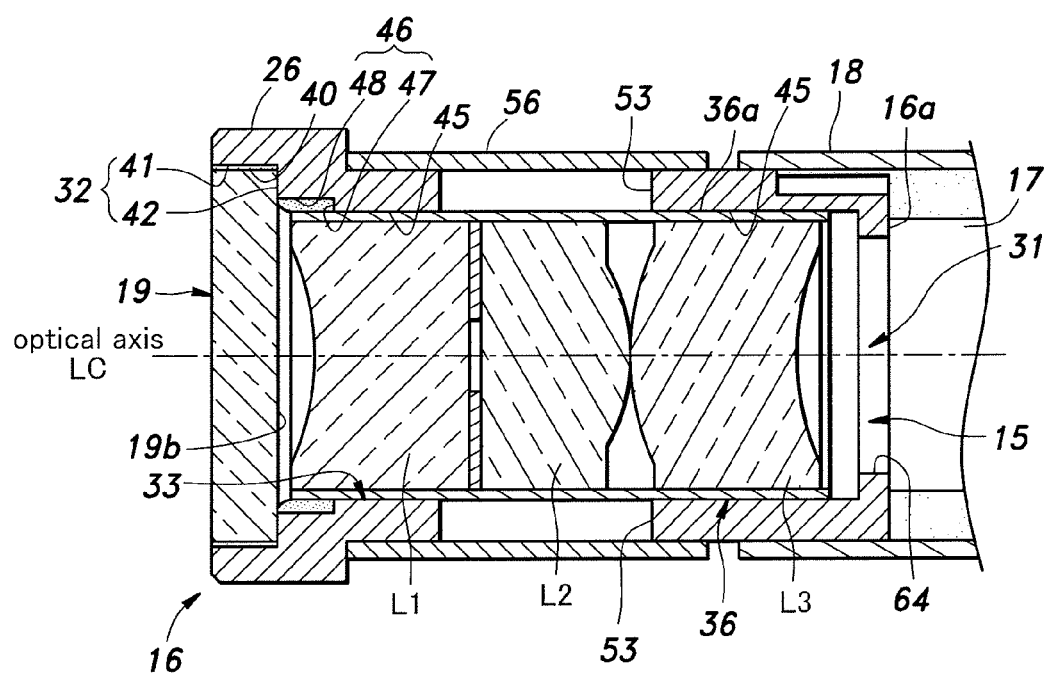
FIG. 5 is a horizontal cross-sectional view of the insertion portion distal end of the endoscope.
Figure 6:
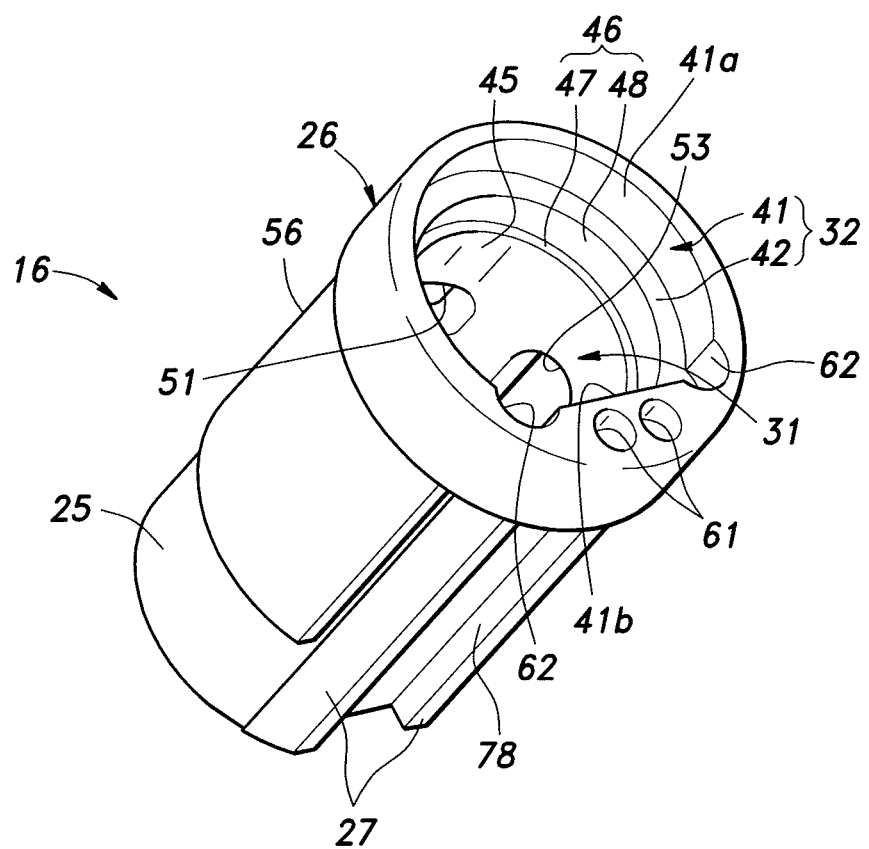
FIG. 6 is a perspective view of an optical element holder (lens holder) with a holder cover mounted thereto.

FIG. 3, FIG. 4 and FIG. 5 are respectively an exploded perspective view, a vertical cross-sectional view and a horizontal cross-sectional view of the insertion portion distal end 12 of the endoscope 2, and FIG. 6 is a perspective view of the lens holder 16 with a holder cover 56 mounted thereto.

As shown in FIG. 3, the lens holder 16 includes a substantially tubular holder main body 25, a flange 26 that extends out radially from the periphery of the front end portion of the holder main body 25 and a bottom wall 27 provided below the holder main body 25 to support the same. These parts are formed integrally of a highly rigid material (metal, rigid resin, etc.).

As shown in FIGS. 4 to 6, the lens holder 16 is provided with a cylindrical hole 31 extending through the lens holder 16 in the fore and aft direction, and this cylindrical hole 31 defines an internal space (substantially cylindrical space) of the lens holder 16. The cylindrical hole 31 is shaped to form a cover glass fitting portion (closure member fitting portion) 32 to which the cover glass 19 is fixed in a fitted state, and a lens barrel fitting portion 33 which has a smaller diameter than that of the cover glass fitting portion 32 and into which the lens unit 15 is fitted. In the lens unit 15, multiple (in this embodiment, three) optical lenses L1-L3 each made of an optical material (glass, resin, etc.) and having the same diameter and a diaphragm member 35 are received in a metallic lens barrel 36, which is a tubular lens frame constituting an outer shell of the lens unit 15, such that the optical lenses L1-L3 and the diaphragm member 35 are in close contact with each other in the direction of an optical axis LC.

As shown in FIGS. 4 and 5, the cover glass fitting portion 32 is defined inside the flange 26 forming a distal end portion of the lens holder 16 and is formed as a substantially concave part shaped to be able to receive the cover glass 19 therein. The cover glass 19 fitted into the cover glass fitting portion 32 is fixed thereto by a bonding agent 40, whereby imaging light passes through the cover glass 19 into the lens holder 16. In the present embodiment, the cover glass 19 is used for the purpose of protecting the lens unit 15 in the lens holder 16, but the present invention is not limited thereto and the cover glass 19 may have a lens function of refracting the incident light to diverge or converge the light.

Various known bonding agents may be used as the bonding agent 40, but a thermosetting resin such as an epoxy resin or an acrylic resin may be preferably used. Alternatively, a UV curable resin may be used as the bonding agent 40. It is to be noted that the term "bonding agent" in the present specification is not only used in a strict sense to refer to a material used to cause a surface of a solid object to adhere to a surface of another solid object but may also be used in a broader sense to refer to a material used to bond any two objects.

Further, the cover glass fitting portion 32 includes a first circumferential wall (axial wall) 41 disposed to surround the optical axis LC and a first end wall (annular shoulder surface) 42 that extends inward from a rear edge of the first circumferential wall 41 in a plane that intersects the optical axis LC substantially perpendicularly. The first circumferential wall 41 and the first end wall 42 are provided to be in contact with or in the vicinity of an outer circumferential surface 19a (see FIG. 3) and a part (outer peripheral part) of a rear surface 19b of the cover glass 19, respectively.

The lens barrel fitting portion 33 is defined inside the flange 26 and the holder main body 25 at the rear of the cover glass fitting portion 32 and has a substantially cylindrical shape such that the lens barrel 36 can be fitted therein. The lens barrel fitting portion 33 includes a second circumferential wall 45 disposed to surround the optical axis LC and an increased diameter portion 46 provided on a front end side of the second circumferential wall 45. The second circumferential wall 45 is provided to be in contact with or in the vicinity of an outer circumferential surface 36a of the lens barrel 36 of the lens unit 15 fitted into the lens barrel fitting portion 33. It is to be noted that, even after being fitted into the lens barrel fitting portion 33, the lens unit 15 is allowed to move in the fore and aft direction during later-described position adjustment prior to fixing of the position.

The increased diameter portion 46 includes a second end wall 47 extending outward from a front edge of the second circumferential wall 45 and located on a plane intersecting the optical axis LC substantially perpendicularly and a third circumferential wall 48 extending forward from an outer peripheral edge of the second end wall 47 to the first end wall 42 and surrounding the optical axis LC. The third circumferential wall 48 surrounds at least a distal end portion of the lens unit 15 (lens barrel 36) so as not to be in contact therewith. As described in detail later, in such a structure, a space that is defined by the increased diameter portion 46 around the lens barrel 36 to axially adjoin the first end wall 42 (or the cover glass fitting portion 32) serves as a bonding agent reservoir that can accommodate a portion (excess portion) of the bonding agent 40 used to fix the cover glass 19 when the cover glass 19 is mounted to the lens holder 16.

An upper portion of the holder main body 25 is provided with a position fixing hole 51 having a substantially elongated circular shape extending in the circumferential direction (see FIGS. 3 and 4). Further, provided on the left and right sides of the holder main body 25 are position adjustment holes (side openings) 53 (see FIG. 5) for adjustment of the position of the lens unit 15. The left and right position adjustment holes 53 each have a substantially elongated circular shape extending in the axial direction and are disposed at positions symmetric to each other. The lens unit 15 is fixed to the lens holder 16 by a bonding agent 55 injected into the position fixing hole 51 after adjustment of the position of the lens unit 15.

Further, a metallic (stainless steel) holder cover 56 is mounted to the outer circumferential surface of the holder main body 25 of the lens holder 16. As shown in FIG. 3, the holder cover 56 consists of a tubular member with a part thereof cut away so that the holder cover 56 is substantially in the shape of letter C as seen in the fore and aft direction and covers the outer circumference of the holder main body 25 to close at least the position fixing hole 51 and the position adjustment holes 53. The holder cover 56 has an inner diameter equal to or slightly smaller than the outer diameter of the holder main body 25. The front edge of the holder cover 56 is connected with a rear face of the flange 26 of the lens holder 16. The left and right lower edges of the holder cover 56 are respectively connected with the left and right edges of the bottom wall 27.

Further, as shown in FIG. 3 and FIG. 6, the flange 26 is provided with a pair of illumination windows 61 arranged side by side in the lateral direction below the cover glass fitting portion 32. These illumination windows 61 each have a substantially circular shape as seen in the front view, and the light output from a light source (not shown in the drawings) provided on the side of the video processor 3 and transmitted via optical fibers (not shown in the drawings) is emitted forward through the illumination windows 61 toward an object to be imaged. In addition, the flange 26 is configured such that the first circumferential wall 41 defining the cover glass fitting portion 32 has an upper circular portion 41a and a lower straight portion 41b (see FIG. 6) so as to be in conformity with the shape of the outer circumferential surface 19a of the cover glass 19. At left and right boundaries between the circular portion 41a and the straight portion 41b are formed a pair of left and right recesses 62, each of which has a substantially semicircular shape projecting out in the radially outward direction as seen in the front view and extends axially over the axial extent of the first circumferential wall 41; namely, each recess 62 extends from the first end surface 42 to the front end of the lens holder 16 and opens out in the front end face. The left and right recesses 62 are provided to sandwich the pair of illumination windows 61 so as not to interfere with the arrangement of the illumination windows 61.

As will be described in detail later, when the cover glass 19 is mounted to the cover glass fitting portion 32, the circular portion 41a and the straight portion 41b (see FIG. 6) of the first circumferential wall 41 of the cover glass fitting portion 32 provide a bonding surface (bonding area) that is in contact with or in the vicinity of the outer circumferential surface 19a of the cover glass 19, while the recesses 62 of the first circumferential wall 41 form a surface (spaced area) that is more distant from the outer circumferential surface 19a of the cover glass 19 than the bonding surface provided by the circular portion 41a and straight portion 41b are.

The image sensor 17 is embodied as a CCD (Charge Coupled Device) or a CMOS (Complementary Metal-Oxide Semiconductor) which, as shown in FIG. 3, is substantially rectangular in shape as seen in a front view (as seen in the fore and aft direction) and small in size (in this embodiment, each side of the rectangle is 1 mm). As shown in FIG. 4, the image sensor 17 is fixed such that the image sensor 17 is in contact with a rear wall 16a of the lens holder 16. The rear wall 16a of the lens holder 16 is provided with a through-hole 64 that is in communication with the lens barrel fitting portion 33. Thereby, the light entering through the cover glass 19 passes through the optical lenses L1-L3 in the lens barrel 36 and through the through-hole 64, and forms an image on the light receiving surface of the image sensor 17. Attached to a rear part (rear face side) of the image sensor 17 is a circuit board 65, on which a drive circuit for the image sensor 17, etc. are provided. The circuit board 65 has a slightly smaller outer profile than the image sensor 17 as seen in the fore and aft direction. Further, a rear part (rear face side) of the circuit board 65 is electrically connected with a distal end portion 63 of the transmission cable 11 by soldering.

As shown in FIG. 3, the rear cover 18 has a shape of a cylinder with a flat bottom such that the rear cover 18 is substantially in the shape of letter D as seen in the fore and aft direction. The rear cover 18 has an upper cylindrical wall 71 and a lower flat bottom wall 72. The cylindrical wall 71 of the rear cover 18 is provided with a pair of left and right cutout portions 73 each opening out in the front end of the rear cover 18, and the bottom wall 72 is provided with a cutout portion 74 also opening out in the front end of the rear cover 18. The left and right cutout portions 73 each have a substantially rectangular shape and are arranged at positions respectively corresponding to the upper left and right corners 17a of the image sensor 17. As shown in FIG. 4, the distal end portion 63 of the transmission cable 11 which is electrically connected with the image sensor 17 is inserted through a substantially circular cable insertion hole 75 formed in the rear wall 18a of the rear cover 18. The inside of the rear cover 18 is filled with a bonding agent 76 for sealing, such that the bonding agent 76 covers the image sensor 17, the circuit board 65 and the distal end portion 63 of the transmission cable 11 (a part for electrical connection with the image sensor 17).

The rear cover 18 is mounted to a rear portion of the lens holder 16. In the state where the rear cover 18 has been mounted, a rear portion of the holder main body 25 is received in a space defined by the cylindrical wall 71 of the rear cover 18, while the front end of the bottom wall 72 of the rear cover 18 abuts a stepped part 77 (see FIG. 4) provided in a lower portion of the lens holder 16. The stepped part 77 is formed by cutting away a lower part of the rear wall 16a of the lens holder 16 including the bottom wall 27 in the forward direction. It is to be noted that a concave groove 78 extending in the fore and aft direction is formed on an underside of the bottom wall 27 (see FIG. 6). The front end of the groove 78 is in communication with the illumination windows 61 in the flange 26 and optical fibers not shown in the drawings are arranged in the groove 78.

Figure 7A:
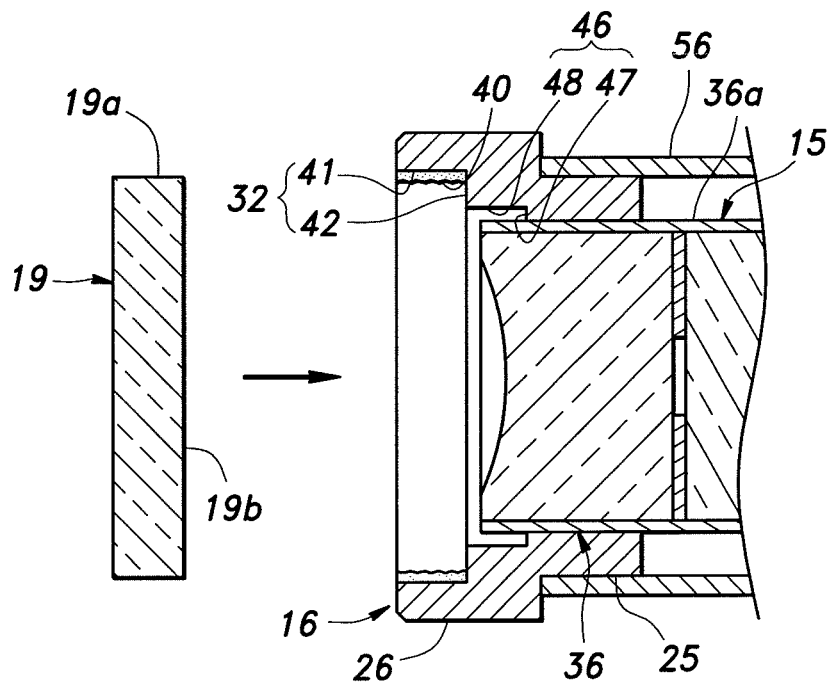
FIGS. 7A and 7B are explanatory diagrams for showing a process of mounting a cover glass to the lens holder.
Figure 7B:
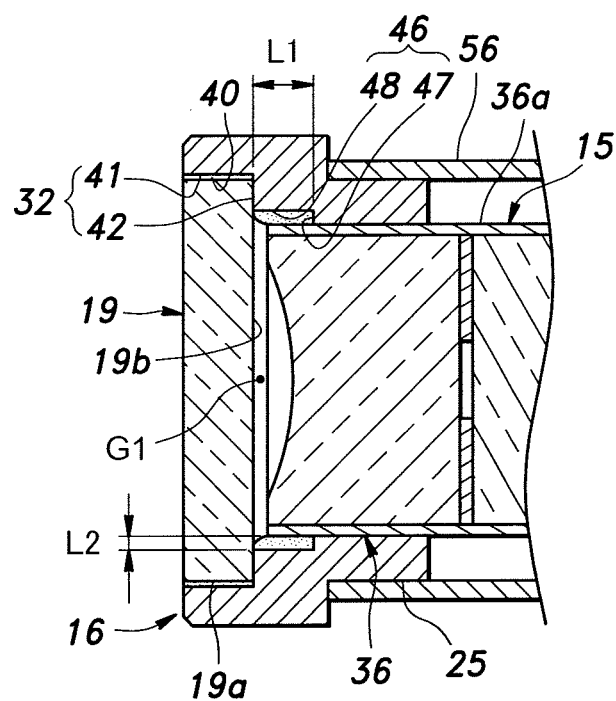

FIGS. 7A and 7B are explanatory diagrams for showing a process of mounting the cover glass 19 to the lens holder 16. In the following, a description will be given of a series of processes of assembling the insertion portion distal end 12 of the endoscope 2 in the present embodiment, including the mounting process of the cover glass 19. The assembly of the insertion portion distal end 12 is basically performed manually by a worker using a microscope together with adjustment jigs, etc.

<Mounting Process of Image Sensor 17>

In the mounting process of the image sensor 17, by operating an XYZ stage (not shown in the drawings) the worker adjusts the position of the image sensor 17 (see FIG. 3) relative to the lens holder 16 in the vertical direction and in the fore and aft direction to bring the image sensor 17 in contact with the lens holder 16. Then, the worker further adjusts the position of the image sensor 17 such that the center of the image sensor 17 is aligned with the optical axis LC. After the positioning of the image sensor 17 is completed, the worker applies a bonding agent along the top, right and left front edges of the image sensor 17 to fix the image sensor 17. A UV curable resin may be used as the bonding agent.

<Mounting Process of Lens Barrel 36>

In the mounting process of the lens barrel 36, the worker assembles the lens unit 15 in advance by setting the optical lenses L1-L3, etc. in the lens barrel 36. The worker pinches the lens unit 15 with a pair of tweezers or the like and inserts the lens unit 15 into the lens holder 16. At this time, the lens unit 15 is fitted into the lens barrel fitting portion 33.

A pair of adjustment jigs (not shown in the drawings) are used to adjust the position of the lens barrel 36. The worker presses the adjustment jigs onto respective parts of the outer circumferential surface of the lens barrel 36 exposed by the two position adjustment holes 53 (see FIG. 3) provided to the lens holder 16, so that the adjustment jigs hold the lens barrel 36 with a frictional force caused by the pressing. In that state, by slightly moving the adjustment jigs in the direction of the optical axis LC of the lens barrel 36 (fore and aft direction), the worker can adjust the position of the lens barrel 36 in the lens holder 16. This adjustment is performed such that the incident light from an object to be imaged is focused on the imaging surface of the image sensor 17 (namely, focus adjustment is carried out).

In the present embodiment, configuration is made such that the adjustment jigs interpose the lens barrel 36 therebetween and hold the lens barrel 36 from both lateral sides. Specifically, the two position adjustment holes 53 through which the respective adjustment jigs are inserted are provided at positions point-symmetric to each other with respect to the optical axis LC. Thus, the adjustment jigs inserted through these position adjustment holes 53 also contact the outer circumferential surface of the lens barrel 36 at positions point-symmetric to each other with respect to the optical axis LC. In this way, the pressing forces from the adjustment jigs act in the radial direction toward the optical axis LC and no undesired rotational force or the like is applied to the lens barrel 36, and therefore, undesired deformation or the like of the lens barrel 36 can be avoided.

After the positioning of the lens barrel 36 is completed, the bonding agent 55 (see FIG. 4) is injected into the position fixing hole 51 provided in the upper side of the lens holder 16 while the lens barrel 36 is kept held by the adjustment jigs (namely, while the position of the lens barrel 36 relative to the lens holder 16 is maintained). Since the bonding agent 55 is exposed by the position fixing hole 51, a UV curable resin can be used as the bonding agent 55.

After the bonding agent 55 has cured, the adjustment jigs are removed from the position adjustment holes 53. After the removal of the adjustment jigs, a bonding agent may be injected into the position adjustment holes 53 similarly to the position fixing hole 51. By doing so, it is possible to cause the lens barrel 36 to adhere to a large area of the lens holder 16 in the circumferential direction, thereby fixing the lens barrel 36 reliably and improving the mechanical strength of the lens barrel 36 itself.

<Mounting Process of Cover Glass 19>

In the mounting process of the cover glass 19, as shown in FIG. 7A, the worker applies the bonding agent 40 to the first circumferential wall 41 of the cover glass fitting portion 32 using a fine brush or the like, and thereafter, as shown in FIG. 7B, fits the cover glass 19 into the cover glass fitting portion 32.

For example, the worker causes a suction cup to adhere to the front surface of the cover glass 19 and then pushes it into the cover glass fitting portion 32 to which the bonding agent 40 has been applied. At this time, a portion (excess portion) of the bonding agent 40 applied to the first circumferential wall 41 is pushed inward by an outer peripheral part of the cover glass 19, and moves along the first end wall 42 to enter the increased diameter portion 46 (more precisely, the annular space defined by the increased diameter portion 46 around the outer circumference of the lens barrel 36). This prevents the bonding agent 40 from entering the optical path forming part at the rear of the cover glass 19 (namely, an optical path between the cover glass 19 and the lens unit 15 disposed behind the cover glass 19) without reducing the performance of the bonding agent 40 to seal the opening of the lens holder 16.

It is to be noted that, in a case where the amount of the excess portion of the bonding agent 40 is small, the increased diameter portion 46 is not filled with the bonding agent 40. However, the increased diameter portion 46 has an advantage that it makes it easy to achieve an appropriate amount of the bonding agent 40 to be applied such that at least the outer circumferential surface 36a of the lens barrel 36 and the inner circumferential surface of the increased diameter portion 46 (namely, third circumferential wall 48) are bonded to each other by the bonding agent 40, whereby stable fixing of the lens barrel 36 (the lens unit 15) is achieved.

When the cover glass 19 is mounted, the lens barrel 36 has been already inserted into the lens holder 16, and this somewhat restricts the exit of air from the cylindrical hole 31 through the rear end thereof. However, with use of a bonding agent having a relatively low viscosity (high fluidity), the air remaining in a gap G1 in front of the lens holder 16 or the like moves outward and exits to the outside through the recesses 62 provided at two positions on the periphery of the cover glass fitting portion 32.

In other words, the lens holder 16 is configured such that, when the cover glass 19 is mounted, the recesses 62 serve as an air vent, preventing the bonding agent 40 from being pushed out by the air moving out through the space between the outer circumferential surface 19a of the cover glass 19 and the first circumferential wall 41 (circular portion 41a and straight portion 41b) of the cover glass fitting portion 32. It is to be noted that the recesses 62 formed in the first circumferential wall 41 may be altered in shape, size and positions in various ways so long as they constitute an air vent.

Thus, the worker can mount the cover glass 19 to the cover glass fitting portion 32 easily, and the cover glass 19 once mounted will not be pushed out forward. It is to be noted that a gap (clearance) between the cover glass fitting portion 32 and the cover glass 19 when the cover glass 19 is fitted into the cover glass fitting portion 32 such that they contact each other on one side is set to 20 to 65 μm.

In the present embodiment, the lens barrel 36 has an outer diameter of about 1 mm, and the circular portion (excluding the cutout portion) of the cover glass 19 has an outer diameter of about 1.4 mm. With regard to the size of the bonding agent reservoir formed by the increased diameter portion 46, it has a length L1 of about 180 to 230 μm in the direction of the optical axis and a width L2 of about 50 to 80 μm in the radial direction. Further, the gap G1 between the front end of the lens holder 16 and the rear surface 19b of the cover glass 19 is about 30 to 80 μm. Owing to the presence of the gap G1, it is ensured that the cover glass 19 fitted into the cover glass fitting portion 32 of the lens holder 16 does not interfere with the lens unit 15 (lens barrel 36) received in the lens holder 16.

It is to be noted that though FIG. 7A shows an example in which the bonding agent 40 is applied to the first circumferential wall 41, the worker may apply the bonding agent 40 to the first end wall 42 also, if necessary. Further, though not shown in FIG. 7B, a layer of the bonding agent 40 may also be formed between the surface of the first end wall 42 and the cover glass 19 similarly to between the surface of the first circumferential wall 41 and the cover glass 19.

In the aforementioned mounting process of the cover glass 19, when the amount of application of the bonding agent 40 is insufficient, the worker may inject an additional bonding agent through the recesses 62 (see FIG. 3 and FIG. 6) by use of a bonding agent dispenser (needle) or the like not shown in the drawings. The injected bonding agent is caused to move inward due to capillary action between the cover glass 19 (outer circumferential surface 19a) and the first circumferential wall 41. In a case where the amount of the bonding agent 40 is excessive and the bonding agent 40 is discharged to the outside of the cover glass 19, the recesses 62 serve as a bonding agent reservoir as well.

As described in the foregoing, in the present embodiment, the opening (imaging window) of the lens holder 16 on the distal end side is closed by the cover glass 19 airtightly. As the cover glass 19 is light-transmissive (in this embodiment, transparent), a UV curable resin can be used as the bonding agent 40, and this can reduce the time required for the curing.

<Mounting Process of Rear Cover 18>

In the mounting process of the rear cover 18, as a preprocessing, a bonding agent 76 is applied to cover the image sensor 17, the circuit board 65 and the distal end portion 63 of the transmission cable 11, which are positioned behind the rear end of the holder main body 25 of the lens holder 16. Further, the interior of the rear cover 18 is appropriately filled with the bonding agent 76. The bonding agent 76 has such a high viscosity that the bonding agent 76 can cover at least the image sensor 17, the circuit board 65 and the distal end of the transmission cable 11, and is used for the purpose of providing a seal for substantially preventing entrance of moisture into the section at the rear of the image sensor 17. Various known bonding agents may be used as the bonding agent 76, but a thermosetting resin such as an epoxy resin or an acrylic resin may be preferably used.

After the preprocessing, the rear cover 18 is fitted over the rear portion of the lens holder 16, yielding the state shown in FIG. 2 and FIG. 4. At this time, the front end of the bottom wall 72 of the rear cover 18 abuts the vertical surface of the stepped part 77 of the lens holder 16, and this regulates the position of the rear cover 18 in the fore and aft direction. Further, the upper surface of a front end portion of the bottom wall 72 abuts the horizontal surface of the stepped part 77, and this regulates the position change in the upward direction. The cutout portions 73 and the cable insertion hole 75 of the rear cover 18 serve as an air vent, making it possible to readily fill the interior of the rear cover 18 with the bonding agent 76.

<Mounting Process of Holder Cover 56>

In the mounting process of the holder cover 56, the worker supports the outer circumferential surface of the holder cover 56 with a mounting jig not shown in the drawings, adjust the orientation of the holder cover 56 so that the opening side thereof faces upward, and applies a bonding agent to the inner circumferential surface of the holder cover 56. As the bonding agent, a bonding agent consisting of a thermosetting resin such as an epoxy resin or an acrylic resin may be preferably used. Subsequently, the worker turns the holder cover 56 upside down so that the opening side thereof opposes the position fixing hole 51 formed in the lens holder 16. Then, the worker moves down the mounting jig supporting the holder cover 56 to press the holder cover 56 against the lens holder 16 from above (in the radial direction).

When pressed against the lens holder 16, the opening side of the C-shaped holder cover 56 undergoes elastic deformation such that it widens in the lateral direction. It is to be noted that the curvature of the inner circumferential surface of the holder cover 56 in the circumferential direction when applied no external force is set to be substantially equal to the curvature of the outer circumferential surface of the lens holder 16 in the circumferential direction. When the worker further presses down the holder cover 56 so that the lens holder 16 is received in the holder cover 56, the widened holder cover 56 tends to return to its original state, causing the entirety of the inner circumferential surface of the holder cover 56 to grasp the outer circumferential surface of the lens holder 16. As a result, the holder cover 56 is attached to the lens holder 16 by the restoring force resulting from its elastic deformation.

Although the present invention has been described in terms of preferred embodiments thereof, these embodiments are mere examples and the present invention is not limited by the embodiments. For instance, the insertion portion of the endoscope according to the present invention is not limited for use as a flexible scope, and may be used as a rigid scope. Further, the shape and size of the increased diameter portion provided to the holder member can be altered or varied in various ways so long as an excess portion of the bonding agent for fixing the closure member can be accommodated therein.

Figure 8:
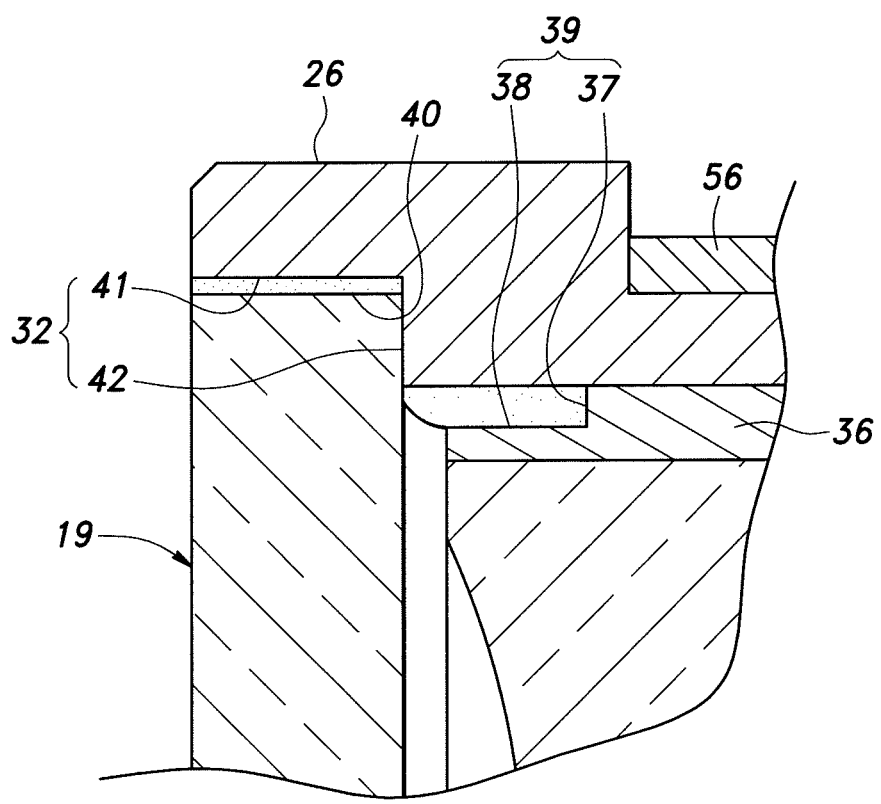
FIG. 8 is a partial vertical cross-sectional view of a modified embodiment of the insertion portion distal end of the endoscope.

Further, in the foregoing embodiment, the annular space defined around the lens barrel 36 and serving as a bonding agent reservoir was created by the increased diameter portion 46 on the inner circumferential surface of the lens holder 16. However, the present invention is not limited to such a structure. FIG. 8 is a partial vertical cross-sectional view of a modified embodiment of the insertion portion distal end 12 of the endoscope 2. In FIG. 8, the parts similar to those in FIG. 4 are denoted by same reference numerals. In the embodiment shown in FIG. 8, the increased diameter portion 46 is not provided on the inner circumferential surface of the lens holder 16 but instead, a reduced diameter portion 39 is provided on the outer peripheral surface of the front end portion of the lens barrel 36. The reduced diameter portion 39 includes an outer circumferential wall 38 extending over a certain axial length from the front (distal) end of the lens barrel 36 and having a diameter smaller than that of the axially rearward adjoining portion of the lens barrel 36 so that an end wall (shoulder surface) 37 is formed between the reduced diameter portion 39 and the axially rearward adjoining portion of the lens barrel 36. In this arrangement also, an annular space that can accommodate an excess amount of the bonding agent for fixing the lens cover 19 is defined between the outer circumferential surface of the front end portion of the lens barrel 36 and the opposing inner circumferential surface of the lens holder 16.

It is also to be noted that not all of the structural elements of the endoscope and the endoscope system shown in the foregoing embodiments are necessarily indispensable, and they may be selectively used as appropriate without departing from the spirit of the present invention.

The endoscope and the endoscope system according to the present invention make it possible, in a structure where a light-transmissive closure member is fixed by a bonding agent to a distal end (front) opening of an insertion portion that is to be inserted into an inside of an object to be observed, to prevent entrance of the bonding agent into an optical path forming part defined at the rear of the closure member without reducing the performance of the bonding agent to seal the opening, and thus, are useful as an endoscope and an endoscope system for capturing an image of an inside of an object that cannot be observed directly from outside.

What is claimed is:

1. An endo scope having an insertion portion to be inserted into an object to be observed, comprising:
   a tubular holder member mounted to the insertion portion and having an open front end portion including a shoulder surface surrounded by an axial wall;
   a lens barrel received in the holder member;
   an objective lens system having an optical axis and held by the lens barrel; and
   a light-transmissive closure member fitted into a front opening defined by the axial wall of the holder member and the shoulder surface, and fixed to the front opening by a bonding agent interposed between an outer circumferential surface of the closure member and an opposing inner circumferential surface of the open front end portion of the holder member, wherein the shoulder surface extends from the axial wall in a direction perpendicular to the optical axis, a space axially adjoining the shoulder surface in a direction along the optical axis is defined between an outer circumferential surface of a front end portion of the lens barrel and an opposing inner circumferential surface of the holder member, the space is provided radially inward of the shoulder surface, and the closure member fitted into the front opening is fixed to the shoulder surface.

2. The endoscope according to claim 1, wherein the space is defined by an increased diameter portion provided on the inner circumferential surface of the holder member.

3. The endoscope according to claim 1, wherein the space is defined by a reduced diameter portion provided on the outer circumferential surface of the front end portion of the lens barrel.

4. The endoscope according to claim 1, wherein at least a portion of the bonding agent is provided in the space between the outer circumferential surface of the front end portion of the lens barrel and the opposing inner circumferential surface of the holder member and bonds the outer circumferential surface of the front end portion of the lens barrel to the opposing inner circumferential surface of the holder member.

5. The endoscope according to claim 1, wherein the axial wall of the holder member is provided with at least one recess on an inner circumferential surface thereof such that the at least one recess extends over an axial extent of the axial wall.

6. The endoscope according to claim 1, wherein the outer circumferential surface of the closure member and the opposing inner circumferential surface of the open front end portion of the holder member are configured to engage each other so as to prevent rotation of the closure member relative to the holder member.

7. The endoscope according to claim 1, wherein the lens barrel is received in the holder member such that a front end of the lens barrel is displaced axially rearward from the shoulder surface of the holder member and a gap is provided between a rear surface of the closure member abutting the shoulder surface and the front end of the lens barrel.

8. The endoscope according to claim 1, wherein the holder member is provided with a side opening to expose an outer circumferential surface of the lens barrel such that the lens barrel in the holder member is accessible for position adjustment.

9. An endoscope system, comprising:
the endoscope according to claim 1; and
an image processing device that processes an image provided by the endoscope.

10. The endoscope according to claim 1, wherein the closure member fitted into the front opening is bonded to the shoulder surface by at least a portion of the bonding agent that is interposed between the closure member and the shoulder surface.

* * * * *